United States Patent [19]

Inagawa et al.

[11] 4,352,881
[45] Oct. 5, 1982

[54] METHOD OF MEASURING CREATINE KINASE ACTIVITY

[75] Inventors: Masanobu Inagawa; Toshiyuki Sai; Seiichi Kawarabuki; Naoto Miwa, all of Ibaraki, Japan

[73] Assignee: Mitsubishi Petrochemical Co., Ltd., Tokyo, Japan

[21] Appl. No.: 302,868

[22] Filed: Sep. 16, 1981

Related U.S. Application Data

[63] Continuation of Ser. No. 101,381, Dec. 7, 1979, abandoned.

[30] Foreign Application Priority Data

Dec. 12, 1978 [JP] Japan .................................. 53-153311

[51] Int. Cl.³ .............................................. C12Q 1/50
[52] U.S. Cl. ......................................... 435/17; 435/26
[58] Field of Search .................. 435/15, 17, 26, 189, 435/194, 805, 810; 252/408 R; 424/2; 23/230 B

[56] References Cited

U.S. PATENT DOCUMENTS 3,929,580 12/1975 Forgione et al. ...................... 435/17
4,012,286 3/1977 Sanderson et al. .................... 435/17
4,162,194 7/1979 Pierre et al. ............................ 435/26

OTHER PUBLICATIONS

Cohn, M.; Biochimica et Biophysica Acta; vol. 20, pp. 92–99 (1956).
Koutras, J. A. et al.; *Journal of Clinical Investigation;* vol. 23, No. 2, pp. 323–331 (1964).
Dixon, M. et al., "Enzymes", Academic Press Inc. Pub., N.Y.; p. 569 (1964).

*Primary Examiner*—Benoit Castel
*Attorney, Agent, or Firm*—Sughrue, Mion, Zinn, Macpeak & Seas

[57] ABSTRACT

A method and composition for use therein for measuring the activity of creatine kinase (hereinafter referred to as "CK") having good storage stability is disclosed. More particularly, a composition for measurement of CK activity which comprises as main components phosphoglycerate kinase (hereinafter referred to a "PGK") which catalyzes the following reaction 2 and glyceraldehyde-3-phosphate dehydrogenase (hereinafter referred to as "GAPDH") which catalyzes the following reaction 3. Reaction 1 is catalyzed by the creatine kinase.

Reaction 1
  Creatinephosphate + Adenosine-5'-diphosphate (hereinafter referred to as "ADP") ⇌ Creatine + Adenosine-5'-triphosphate (hereinafter referred to as "ATP")

Reaction 2
  ATP + 3-Phosphoglycerate ⇌ ADP + 1,3-Diphosphoglycerate

Reaction 3
  1,3-Diphosphoglycerate + Reduce β-nicotinamideadenine dinucleotide (hereinafter referred to as "NADH") ⇌ Glyceraldehyde-3-phosphate + β-nicotinamideadenine dinucleotide (hereinafter referred to as "NAD") + Inorganic phoshate 4 Claims, 2 Drawing Figures

METHOD OF MEASURING CREATINE KINASE ACTIVITY

This is a Continuation of application Ser. No. 101,381, filed Dec. 7, 1979, now abandoned.

BACKGROUND OF THE INVENTION

1. Field of the Invention

The present invention relates to a method for measuring creatine kinase activity. More particularly, it relates to a method employing a composition containing phosphoglycerate kinase (PGK) and glyceraldehyde-3-phosphate dehydrogenase (GAPDH).

2. Description of the Prior Art

The activity of CK is one of the indices of clinical diagnosis, for example, progressive muscular dystrophy and myocardial infarction. Hitherto, CK activity has generally been measured using as a coupling enzyme for CK a reagent comprising hexokinase and glucose-6-phosphate dehydrogenase as main components (hereinafter referred to as "HK method"). The HK method is based on the following equations (1), (4) and (5). The enzymes which catalyze the reactions of the equations (4) and (5) are hexokinase and glucose-6-phosphate dehydrogenase, respectively.

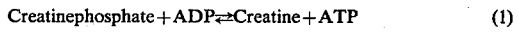

Creatinephosphate + ADP ⇌ Creatine + ATP          (1)

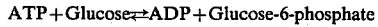

ATP + Glucose ⇌ ADP + Glucose-6-phosphate         (4)

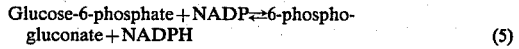

Glucose-6-phosphate + NADP ⇌ 6-phosphogluconate + NADPH      (5)

While the HK method is fairly accurate, the storage stability of hexokinase or glucose-6-phosphate dehydrogenase is inferior and the reagent for the measurement of CK activity can be kept stable only for several hours after preparation. Accordingly, it has been desired to provide coupling enzymes having more excellent storage stability.

Further, in the HK method, reduced glutathione (hereinafter referred to as "GSH") is preferably used. However, when a glutathione reductase (hereinafter referred to as "GR") is present in the test sample, GSH oxidized by some reaction or other is reduced and, at the same time, reduced β-nicotinamideadenine dinucleotide phosphate (hereinafter referred to as "NADPH") formed by a primary reaction is reoxidized to reform oxidative nicotinamideadenine dinucleotide phosphate (hereinafter referred to as "NADP"). Consequently, there is a danger of misjudging the CK activity in the test samples as being low.

As a result of earnest studies directed to improving the above-described disadvantages in the prior method of the measurement, it has been found that if a composition having excellent storage stability comprising PGK and GAPDH as main components is used as a coupling enzyme for measurement of the CK activity, accurate measurement can be carried out without a great influence by GR in the test sample, and thus the present invention has been established.

SUMMARY OF THE INVENTION

The object of the present invention is to provide a method for measurement of the CK activity which comprises PGK and GAPDH as essential components.

DETAILED DESCRIPTION OF THE INVENTION

Figure 1:
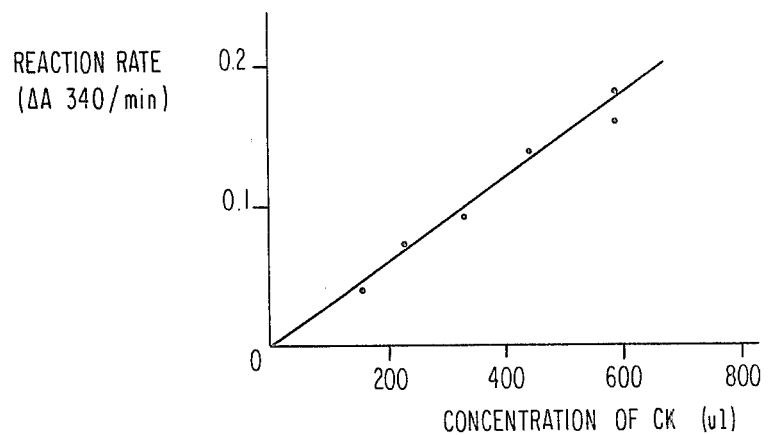
FIG. 1 is a graph showing the relationship between the concentration of CK in a test sample and the decrease in absorbance per minute at 340 nm (i.e., the reaction rate, ΔA 340/min).

The method of measuring CK activity using the composition of the present invention is based on a principle represented by the following reaction equations (1) to (3).

Creatine phosphate + ADP ⇌ Creatine + ATP         (1)

ATP + 3-Phosphoglycerate ⇌ ADP + 1,3-Diphosphoglycerate      (2)

1,3-Diphosphoglycerate + NADH ⇌ Glyceraldehyde-3-phosphate + NAD + Inorganic phosphate       (3)

By carrying out a series of reactions represented by the equations (1) to (3) described above, the CK activity in the test sample which catalyzes the reaction of the equation (1) can be measured by the rate of reduction per unit time of the absorbance of NADH at 334 nm, 340 nm or 366 nm in the equation (3); or by the rate of reduction per unit time of absorbance in visible light by reacting NADH with a color reagent.

The enzyme which catalyzes the reaction of the equation (2) is PGK and that of the equation (3) is GAPDH.

In the method of measurement of the CK activity using the composition of the present invention reagents II to IV described in detail below are used in addition to the composition of the present invention (hereinafter referred to as "reagent I"). The designation of reagents II, III and IV hereinafter is not critical and is simply for the purpose of explaining the present invention in more detail.

Reagent I is the composition used in the method of the present invention and contains PGK and GAPDH as essential components in a buffer solution or as a freeze-dried product. As the buffer, any compound providing a solution having a pH of about 6 to 9 can be used. Examples of the suitable buffers are tris(hydroxymethyl)aminomethane, imidazole, triethanolamine and the like.

Further, a stabilizer may be added to the composition to activate CK and GAPDH such as sulfhydryl compounds like GSH or salts thereof, mercaptoethanol, cysteine or salts thereof, N-acetylcysteine or salts thereof, dithiothreitol, dithioerythritol, thioglycolic acid or salts thereof; and polyhydroxy compounds like glycerine, etc. A chelating agent may also be present. Representative agents are ethylenediaminetetraacetic acid (hereinafter referred to as "EDTA") or salts thereof, glycoletherdiaminetetraacetic acid (hereinafter referred to as "GEDTA") or salts thereof, etc. A sterilizer may also be added such as sodium azide, chlorhexidine or salts thereof.

In addition, lactate dehydrogenase (hereinafter referred to as "LDH") may be added to the composition to prevent any influence by pyruvate which is sometimes contained in a high content in the test sample.

PGK, GAPDH and LDH can be extracted from a variety of organisms containing such enzymes, such as tissues of animals or vegetables and humors thereof or microorganisms, etc., by a conventional method, and they can be used purified by means of salting-out, ion-exchange chromatography, molecular sieve chromatography, affinity chromatography or electrophoresis, etc. Representative sources are yeast, rabbit muscle, pig heart and the like.

The ratio of PGK and GAPDH in the mixture of the present invention is in a range of about 1:0.2 to 2 and preferably about 1:0.3 to 1 (ratio of activity). Further, the total amount of PGK and GAPDH in the buffer solution is about 0.1 to 30 mg/ml (buffer solution).

The amounts of the various components optionally added to the composition as described above are as follows, wherein M represents molar concentration.

| Stabilizer | 0-100mM |
|---|---|
| Chelating agent | 0-10 mM |
| Sterilizer | 0-10 mM |
| LDH | 0-5 (times the PGK activity) |

Reagent II is composed of the following components. Namely, ADP, magnesium salts (e.g., magnesium acetate, magnesium chloride or magnesium sulfate), 3-phosphoglycerate and, as a stabilizer, sulfhydryl compounds such as GSH or salts thereof, mercaptoethanol, cysteine or salts thereof, N-acetylcysteine or salts thereof, dithiothreitol, dithioerythritol, thioglycolic acid or salts thereof, etc. The magnesium salts function as activators for CK. In addition, compounds such as adenosinemonophosphate (hereinafter referred to as "AMP") or diadenosine-pentaphosphate may be added to reagent II to inhibit the reaction of adenylate kinase (myokinase) often found in the test sample. Compounds such as sodium azide, chlorhexidine or salts thereof as a sterilizer and compounds such as EDTA or salts thereof, GEDTA or salts thereof, etc., may also be added as a chelating agent.

Reagent III is a buffer solution capable of maintaining a pH of about 6 to 7.5, such as imidazole for triethanolamine.

Reagent IV is composed of NADH, creatine phosphate and alkaline carbonate or alkaline bicarbonate (reagent IV is stable on the alkaline side and the carbonates are used to maintain reagent IV alkaline). A sterilizer may be contained therein.

When a freeze-dried product is used as reagent I, the reagent I may be combined with the reagent II.

The manner of combining the reagents is not restricted because it varies with the order of addition of the above-described reagents and the kind of diluents. The measurement of the CK activity in the test sample using the composition of the present invention is, for example, carried out by a method which comprises mixing the reagent I with the reagent II, dissolving them in the reagent III diluted with deionized water, and just before the measurement, adding the reagent IV dissolved in deionized water, then adding a test sample while maintaining a suitable temperature (generally 20° to 40° C. ) and measuring a reduction of NADH. Reagents I to IV may be mixed in any order. However, since reagent IV must be alkaline when the reagents are stored for a long period of time it is preferred that reagent IV is mixed with the other reagents immediately before use of the composition. In one embodiment of mixing reagent III is diluted with water, reagents I and II are mixed with the resulting aqueous solution and then reagent IV is mixed with the resulting mixture.

The composition of the mixed reagents and the concentration of the test sample is generally within the following ranges.

| PGK | 0.5-50 μ/ml |
|---|---|
| GAPDH | 0.5-100 μ/ml |
| LDH | 0-250 μ/ml |
| ADP | 0.5-10 mM |
| Creatine phosphate | 10-50 mM |
| Magnesium containing salt | 5-50 mM |
| 3-Phosphoglycerate | 5-50 mM |
| Sulfhydryl compounds | 0.1-100 mM |
| Chelating agents | 0-10 mM |
| Polyhydroxy compounds | 0-0.2 M |
| AMP | 0-25 mM |
| Diadenosine-pentaphosphate | 0-100 μM |
| Sterilizers | 0-10 mM |
| Buffer (pH: 6 to 7.5) | 0.05-0.5 M |
| NADH | 0.1-0.5 mM |
| Alkaline carbonate or alkaline bicarbonate | 0-10 mM |
| Volume fraction of serum in the assay mixture | 0.01-0.5 |

Activities of PGK, GAPDH and LDH are measured by the rate of reduction of NADH at 30° C.

The method of the present invention can also be applied to measurement of creatine phosphate, ADP or ATP.

Creatine kinase activity is generally measured at body temperature (about 35° to 37° C.). If the analysis is conducted at temperature of about 40° C., CK deactivates and measurement is impossible.

The storage stability of PGK and GAPDH used in the present invention is excellent, and thermophilic enzymes obtained from extremely thermophilic microorganisms have remarkably excellent storage stability. As a result the above-described reagents I to IV are stable at low temperatures (the stability increases as the temperature is reduced) to room temperature and can be stored for several months to several years. Further, when the above-described reagents I to III are mixed, the storage stability is excellent. Particularly, when using PGK, GAPDH and LDH obtained from thermophilic microorganisms belonging to Thermus sp. or Bacillus sp. for reagent I, the mixture of the above-described reagents I to III is stable at room temperature for several days to several weeks. Therefore, the CK activity can be measured continuously for several days to several weeks. Further, in the method of measurement of the CK activity using the composition in the present invention, accurate measurement of the CK activity can be carried out without adverse influence by GR in the test sample.

The present invention will now be explained by reference to the following examples. However, the scope of the present invention is not limited to these examples.

EXAMPLE 1

1,250 u of PGK and 625 u of GAPDH prepared by extracting from Thermus thermophilus (ATCC 27634) and purifying by a conventional process were dissolved in 5 ml of a 10 mM buffer solution (pH: 7.5) of tris(hydroxymethyl)-aminomethane containing 10 mM of GSH, 0.2 mM of EDTA and 3 mM of sodium azide to prepare a composition of the present invention.

REFERENCE EXAMPLE 1

The composition obtained in Example 1 was used as the reagent I, and the reagents II to IV were prepared as follows.

Reagent II was prepared by mixing 125μ moles of disodium ADP, 1,250μ moles of magnesium acetate, 1,250μ moles of trisodium 3-phosphoglycerate, 1,250μ moles of GSH, 1,250μ moles of disodium AMP, 625μ moles of EDTA and 380μ moles of sodium azide.

For reagent III, 12.5 ml of 1 M buffer solution of imidazole acetate (pH: 7.0) was prepared.

Reagent IV was prepared by mixing 35μ moles of disodium NADH, 3,750μ moles of disodium creatine phosphate, 240μ moles of sodium bicarbonate, and 30μ moles of sodium azide.

Then, the reagent III was diluted 9.4 times with deionized water, and reagents I and II were dissolved therein. 0.1 ml of the reagent IV dissolved in deionized water to obtain 10 ml of an aqueous solution was added to 1.35 ml of the above-described mixture. 50 μl of a test sample containing CK was added thereto and allowed to stand at a constant temperature (25° to 37° C.) for 3 to 10 minutes. Then, the amount of CK was measured by a reduction rate of absorbance at 340 nm based on the molecular extinction coefficient of NADH at 340 nm.

When the measurement was carried out at 37° C. using a commercially available standard serum, the CK activity was 113 u/l when measured by the method according to the present invention and 110 u/l when measured by the HK method.

REFERENCE EXAMPLE 2

Figure 2:
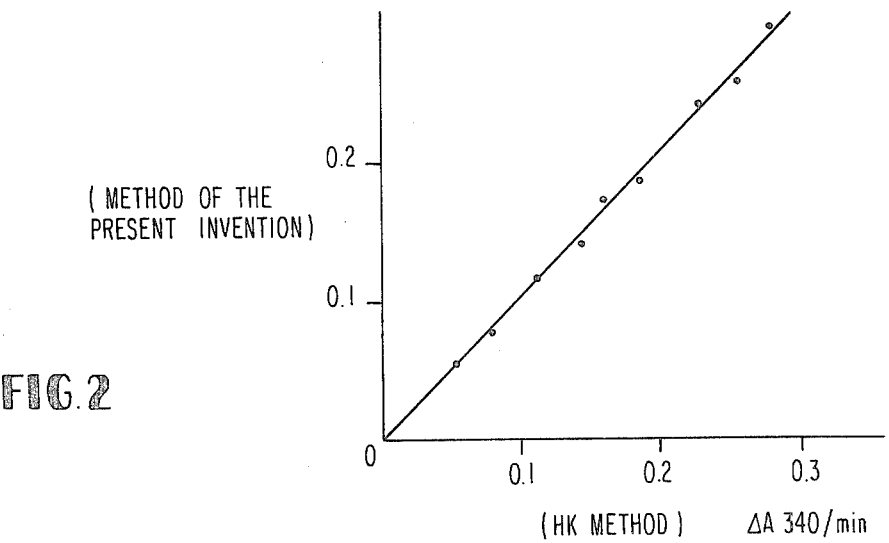
FIG. 2 is a graph showing a comparison between the decrease of absorbance per minute at 340 nm by the HK method and that by the method of the present invention for the same test sample.

When a relationship between the concentration of CK and the reduction in absorbance at 340 nm was examined by varying the amount of CK in the test sample in the same manner as in Example 1, a straight line having a good correlation was obtained. The result obtained as shown in FIG. 1. When the reduction in absorbance obtained by the above-described method and that obtained by the HK method were compared, a good correlation as shown in FIG. 2 was obtained.

EXAMPLE 2

1,250 u of PGK and 625 u of GAPDH prepared by extracting from Bacillus stearothermophilus (ATCC 7954) and purifying by the conventional process were dissolved in 5 ml of 10 mM buffer solution of tris(hydroxymethyl)-aminomethane containing 10 mM of GSH, 0.2 mM of EDTA, 3 mM of sodium azide and 50% by volume based on the total volume of glycerine (pH: 7.5) to prepare a composition of the present invention.

REFERENCE EXAMPLE 3

The concentration of CK in the test sample could be measured in the same manner as in Reference Example 1, except that the composition obtained in Example 2 was used as the reagent I and the reagent III was diluted 9.8 times with deionized water.

REFERENCE EXAMPLE 4

A mixture (A) of the reagents I to III prepared in Reference Example 1, a mixture (B) of the reagents I to III prepared in Reference Example 3, and the reagent IV used in Reference Examples 1 and 3 were each stored at room temperature for 1 week. Then, the mixture (A) and the reagent IV were combined and the mixture (B) and the reagent IV were combined. To each of the mixed solutions was added the same test sample containing CK as used in Example 1, and the CK activity was measured in the same manner as in Example 1. As a result, the same CK activity as obtained in the foregoing corresponding Reference Examples 1 and 3 was obtained.

EXAMPLE 3

2,500 u of PGK prepared by extracting from bakers' yeast and 1,250 u of GAPDH from rabbit muscle were purified by the conventional process. They were mixed and subjected to freeze-drying to prepare a composition of the present invention.

REFERENCE EXAMPLE 5

The concentration of CK in the test sample was measured in the same manner as in Reference Example 1 except that the composition obtained in Example 3 was used as the reagent I. Similar results were obtained to those in Example 1.

REFERENCE EXAMPLE 6

Reagent I obtained in Examples 1 and 2 was stored at room temperature for 1 month and activities of PGK and GAPDH were measured. As a result, it was recognized that the activities were unchanged.

While the invention has been described in detail and with reference to specific embodiments thereof, it will be apparent to one skilled in the art that various changes and modifications can be made therein without departing from the spirit and scope thereof.

What is claimed is:

1. A method for measuring creatine kinase (CK) activity which comprises combining a test sample with the reagents necessary to carry out the following reactions at a pH of about 6 to 7.5:

Creatine phosphate + ADP ⇌ Creatine + ATP    (1)

ATP + 3-Phosphoglycerate ⇌ ADP + 1,3-Diphosphoglycerate    (2)

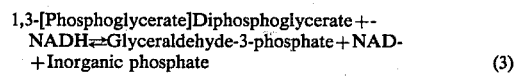

1,3-[Phosphoglycerate]Diphosphoglycerate + NADH ⇌ Glyceraldehyde-3-phosphate + NAD + Inorganic phosphate    (3)

wherein one of those reagents is a composition consisting essentially of 0.5 to 50 u/ml of phosphoglycerate kinase (PGK) and 0.5 to 100 u/ml of glyceraldehyde-3-phosphate dehydrogenase (GAPDH), the ratio of PGK to GAPDH being about 1:0.2 to 2 and the total amount of PGK and GAPDH in the test being about 0.1 to 30 mg/ml, and as another one of said reagents a buffer solution capable of maintaining said pH of about 6 to 7.5, and optically measuring the rate of reduction of NADH optical absorption.

2. The process of claim 1, wherein said NADH absorption is measured at a wavelength of 334 nm, 340 nm or 366 nm.

3. A method for measuring creatine kinase (CK) activity which comprises combining a test sample with a reagent composition necessary to carry out the following reactions:

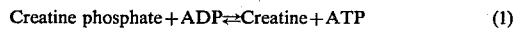

Creatine phosphate + ADP ⇌ Creatine + ATP    (1)

ATP + 3-Phosphoglycerate ⇌ ADP + 1,3-Diphosphoglycerate     (2)

1,3-Diphosphoglycerate + NADH ⇌ Glyceraldehyde-3-phosphate + NAD + Inorganic phosphate     (3)

wherein the reagent composition for carrying out said reactions consists essentially of:

| | |
|---|---|
| PGK | 0.5–50 μ/ml |
| GAPDH | 0.5–100 μ/ml |
| LDH | 0–250 μ/ml |
| ADP | 0.5–10 mM |
| Creatine phosphate | 10–50 mM |
| Magnesium containing salt | 5–50 mM |
| 3-Phosphoglycerate | 5–50 mM |
| Sulfhydryl compounds | 0.1–100 mM |
| Chelating agents | 0–10 mM |
| Polyhydroxy compounds | 0–0.2 mM |
| AMP | 0–25 mM |
| Diadenosine-pentaphosphate | 0–100 μM |
| Sterilizers | 0–10 mM |
| Buffer (to maintain a pH: 6 to 7.5) | 0.05–0.5 M |
| NADH | 0.1–0.5 mM |
| Alkaline carbonate or alkaline bicarbonate | 0–10 mM |
| Volume fraction of serum in the assay mixture | 0.01–0.5, | the ratio of PGK to GAPDH being about 1:0.2 to 2 and the total amount of PGK and GAPDH in the test being about 0.1 to 30 mg/ml, and optically measuring the rate of reduction in NADH optical absorption.

4. A method for measuring creatine kinase (CK) activity which comprises combining a test sample with the reagents necessary to carry out the following reactions at a pH of about 6 to 7.5:

Creatine phosphate + ADP ⇌ Creatine + ATP     (1)

ATP + 3-Phosphoglycerate ⇌ ADP + 1,3-Diphosphoglycerate     (2)

1,3-Diphosphoglycerate + NADH ⇌ Glyceraldehyde-3-phosphate + NAD + Inorganic phosphate     (3)

wherein one of those reagents is a composition consisting essentially of 0.5 to 50 u/ml of phosphoglycerate kinase (PGK), 0.5 to 100 u/ml of glyceraldehyde-3-phosphate dehydrogenase (GAPDH), the ratio of PGK to GAPDH being about 1:0.2 to 2 and the total amount of PGK and GAPDH in the test being about 0.1 to 30 mg/ml, and as another one of said reagents a buffer solution capable of maintaining said pH of about 6 to 7.5, and at least one of a stabilizer, a chelating agent, a sterilizer and lactate dehydrogenase (LDH), and optically measuring the rate of reduction of NADH optical absorption.

* * * * *